US012766129B2

(12) United States Patent
Bar-Or et al.

(10) Patent No.: US 12,766,129 B2
(45) Date of Patent: Oct. 20, 2026

(54) TOPICAL ANTI-INFLAMMATORY AND ANALGESIC COMPOSITIONS AND METHODS OF USE

(71) Applicant: INSIGNIA PHARMACEUTICALS, LLC, Englewood, CO (US)

(72) Inventors: David Bar-Or, Englewood, CO (US); Raphael Bar-Or, Englewood, CO (US)

(73) Assignee: INSIGNIA PHARMACEUTICALS, LLC, Englewood, CO (US)

( * ) Notice: Subject to any disclaimer, the term of this patent is extended or adjusted under 35 U.S.C. 154(b) by 0 days.

(21) Appl. No.: 18/745,075

(22) Filed: Jun. 17, 2024

(65) Prior Publication Data

US 2024/0423957 A1 Dec. 26, 2024

Related U.S. Application Data

(60) Provisional application No. 63/509,085, filed on Jun. 20, 2023.

(51) Int. Cl.

| | |
|---|---|
| ***A61K 31/405*** | (2006.01) |
| ***A61K 9/00*** | (2006.01) |
| ***A61K 31/20*** | (2006.01) |
| ***A61K 47/10*** | (2017.01) |
| ***A61K 47/18*** | (2017.01) |
| ***A61P 19/02*** | (2006.01) |
| ***A61P 29/00*** | (2006.01) |

(52) U.S. Cl.

CPC .......... *A61K 31/405* (2013.01); *A61K 9/0014* (2013.01); *A61K 31/20* (2013.01); *A61K 47/10* (2013.01); *A61K 47/183* (2013.01); *A61P 19/02* (2018.01); *A61P 29/00* (2018.01)

(58) Field of Classification Search

CPC .... A61K 31/405; A61K 9/0014; A61K 31/20; A61K 47/10; A61K 47/183; A61P 19/02; A61P 29/00

See application file for complete search history.

(56) References Cited

U.S. PATENT DOCUMENTS

| | | | | |
|---|---|---|---|---|
| 4,647,453 | A | 3/1987 | Meisner | |
| 8,168,669 | B2 | 5/2012 | Matsumoto et al. | |
| 9,511,016 | B2 | 12/2016 | Oronsky et al. | |
| 9,511,093 | B2 | 12/2016 | Gregory et al. | |
| 9,789,062 | B2 | 10/2017 | Hong et al. | |
| 9,833,460 | B2 | 12/2017 | Shah | |
| 10,500,225 | B2 | 12/2019 | Tauzin | |
| 10,543,242 | B2 | 1/2020 | Stancioiu et al. | |
| 10,668,118 | B2 | 6/2020 | Lynch et al. | |
| 10,668,158 | B2 | 6/2020 | Yang et al. | |
| 11,478,441 | B2 * | 10/2022 | Bar-Or | A61K 31/198 |
| 2005/0176807 | A1 | 8/2005 | Friesen et al. | |
| 2007/0208134 | A1 | 9/2007 | Hunter et al. | |
| 2012/0321597 | A1 | 12/2012 | Hill et al. | |
| 2019/0209446 | A1 | 7/2019 | Han et al. | |
| 2020/0281998 | A1 | 9/2020 | Scharp et al. | |
| 2021/0095254 | A1 | 4/2021 | Frank et al. | |
| 2021/0260010 | A1 | 8/2021 | Hamill et al. | |

FOREIGN PATENT DOCUMENTS

| | | | | | |
|---|---|---|---|---|---|
| EP | 1713464 | A2 | | 10/2006 | |
| KR | 10-0420560 | B1 | | 3/2004 | |
| KR | 20180117259 | | * | 4/2017 | C07K 7/06 |
| KR | 2018117259 | A | * | 10/2018 | A23L 33/18 |
| WO | 2005/077356 | A2 | | 8/2005 | |
| WO | 2019/066505 | A1 | | 4/2019 | |

OTHER PUBLICATIONS

Tsai HY, Yang JF, Chen YB, Guo JL, Li S, Wei GJ, Ho CT, Hsu JL, Chang CI, Liang YS, Yu HS, Chen YK. Acetylation Enhances the Anticancer Activity and Oral Bioavailability of 5-Demethyltangeretin. Int J Mol Sci. Oct. 31, 2022;23(21):13284. (Year: 2022).*

Segarra-Queralt et al. Regulatory network-based model to simulate the biochemical regulation of chondrocytes in healthy and osteoarthritic environments. Sci Rep 12, 3856 (2022). (Year: 2022).*

Namani et al. (2005). From decanoate micelles to decanoic Acid/Dodecylbenzenesulfonate vesicles. Langmuir, 21(14), 6210-6219. (Year: 2005).*

Sun T, Xie R, He H, Xie Q, Zhao X, Kang G, Cheng C, Yin W, Cong J, Li J, Wang X. Kynurenic acid ameliorates NLRP3 inflammasome activation by blocking calcium mobilization via GPR35. Front Immunol. Oct. 13, 2022; 13:1019365. (Year: 2022).*

Mistry, J., & Notman, R. (2024). Mechanisms of the Drug Penetration Enhancer Propylene Glycol Interacting with Skin Lipid Membranes. The Journal of Physical Chemistry B, 128(16), 3885-3897. (Year: 2024).*

(Continued)

*Primary Examiner* — James H Alstrum-Acevedo
*Assistant Examiner* — Pierre Paul Eleniste
(74) *Attorney, Agent, or Firm* — Holland & Hart LLP

(57) ABSTRACT

Various aspects of this disclosure relate to topical anti-inflammatory, analgesic compositions comprising a fatty acid and tryptophan as well as methods of using such compositions. In some specific embodiments, the fatty acid is decanoic acid. Such compositions are generally useful to treat inflammation, and they are specifically useful to treat osteoarthritis.

11 Claims, 5 Drawing Sheets

(56) References Cited

OTHER PUBLICATIONS

Liu L, Zhang W, Liu T, Tan Y, Chen C, Zhao J, Geng H, Ma C. The physiological metabolite α-ketoglutarate ameliorates osteoarthritis by regulating mitophagy and oxidative stress. Redox Biol. Jun. 2023;62:102663. (Year: 2023).*

Machine translation of KR-2018117259-A (Jang Mi Kyeong et al), Oct. 29, 2018, 11 pages. (Year: 2018).*

Shetage, S.S., Traynor, M.J., Brown, M.B. et al. Sebomic identification of sex- and ethnicity-specific variations in residual skin surface components (RSSC) for bio-monitoring or forensic applications. Lipids Health Dis 17, 194 (2018). (Year: 2018).*

Dobler D, Schmidts T, Wildenhain S, Seewald I, Merzhäuser M, Runkel F. Impact of selected cosmetic ingredients on common microorganisms of healthy human skin. Cosmetics. 2019;6(3):45. (Year: 2019).*

Huang WC, Tsai TH, Chuang LT, Li YY, Zouboulis CC, Tsai PJ. Anti-bacterial and anti-inflammatory properties of capric acid against Propionibacterium acnes: A comparative study with lauric acid. Journal of Dermatological Science. 2014;73(3):232-240. (Year: 2014).*

Hajsl M, Hlavackova A, Broulikova K, Sramek M, Maly M, Dyr JE, Suttnar J. Tryptophan Metabolism, Inflammation, and Oxidative Stress in Patients with Neurovascular Disease. Metabolites. May 19, 2020;10(5):208. (Year: 2020).* https://www.ema.europa.eu/en/documents/scientific-guideline/questions-and-answers-propylene-glycol-used-excipient-medicinal-products-human-use_en.pdf (Accessed Sep. 24, 2025) (Year: 2017).*

Wang, Ying-Yue, et al. "In Vitro and in Vivo Evaluations of Topically Applied Capsaicin and Nonivamide from Hydrogels." International Journal of Pharmaceutics, vol. 224, No. 1, Aug. 2001, pp. 89-104. ScienceDirect,1016/S0378-5173(01)00755-4. (Year: 2001).*

"International Search Report and Written Opinion of the International Searching Authority," issued in connection with Int'l Appl. No. PCT/US2024/013250, dated Apr. 16, 2024 (16 pages).

Elmaidomy et al., "Anti-Inflammatory and Antioxidant Properties of Malapterurus electricus Skin Fish Methanolic Extract in Arthritic Rats: Therapeutic and Protective Effects," Marine Drugs, Oct. 14, 2022, vol. 20, No. 639, 22 pages.

Garrett et al., "Long COVID: Is there a kidney link?," Frontiers in Medicine, Apr. 3, 2023, vol. 10, 7 pages.

Grecomoro, G., et. al.,"Therapeutic synergism between hyaluronic acid and dexamethasone in the intra-articular treatment of osteoarthritis of the knee: a preliminary open study", Curr Med Res Opin, vol. 13, Issue. 1, pp. 49-55.

Hajsl et al., "Tryptophan Metabolism, Inflammation, and Oxidative Stress in Patients with Neurovascular Disease," Metabolites, May 19, 2020, vol. 10, No. 208, 19 pages.

Kadir et al., "Evaluation of Chondroprotective Activity of Channa striatus in Rabbit Osteoarthritis Model," BioMed Research International, Jul. 3, 2019, vol. 2019, Article ID 6979585, 11 pages.

Isik et al., "Investigation the fatty acid profile of commercial black cumin seed oils and seed oil capsules: Application to real samples", Journal of Chemical Metrology, Oct. 2019, pp. 53-60, vol. 13, No. 2.

Nayak et al., "Role of Tryptophan in Health and Disease: Systematic Review of the Anti-Oxidant, Anti-Inflammation, and Nutritional Aspects of Tryptophan and Its Metabolites," World Heart Journal, Sep. 2019, pp. 161-178, vol. 11, No. 2.

Stone et al., "Modulation of T cells by tryptophan metabolites in the kynurenine pathway," Trends in Pharmacological Sciences, Jul. 2023, pp. 442-456, vol. 44, No. 7.

Zhang, X., et al., "Caprylic acid suppresses inflammation via TLR4/NF-KB signaling and improves atherosclerosis in ApoE-deficient mice", Nutr Metab, vol. 16, Issue. 40, pp. 1-16.

* cited by examiner

TOPICAL ANTI-INFLAMMATORY AND ANALGESIC COMPOSITIONS AND METHODS OF USE

CROSS REFERENCE TO RELATED APPLICATIONS

This claims priority to and the benefit of U.S. Provisional Patent Application No. 63/509,085, entitled "TOPICAL ANTI-INFLAMMATORY AND ANALGESIC COMPOSITIONS AND METHODS OF USE," filed Jun. 20, 2023, the disclosure of which is hereby incorporated by reference in its entirety.

FIELD OF THE INVENTION

The invention relates to topical compositions comprising a fatty acid and tryptophan that are formulated such that the fatty acid and the tryptophan partition through the skin to reduce inflammation and pain, and promote chondrocyte differentiation in cartilage. Such compositions are generally useful, for example, to treat osteoarthritis.

BACKGROUND

Chronic inflammation and associated pain are generally treatable, for example, with corticosteroids, non-steroidal anti-inflammatory drugs (NSAIDS), and tumor necrosis factor (TNF) inhibitors. Corticosteroids generally bind glucocorticoid and mineralocorticoid receptors, NSAIDs generally inhibit cyclooxygenase enzymes, and TNF inhibitors generally bind and reduce effective concentrations of TNF. Each class of pharmaceutical targets inflammation itself rather than an underlying cause of inflammation. Treating the inflammation itself inhibits pathology caused by the inflammation, but such treatments generally do not reverse harm caused by pathological signaling pathways upstream of the therapeutic target. The identification of novel strategies to treat inflammation is desirable, and strategies that prevent or reverse underlying pathologies could foster a paradigm shift in how physicians manage inflammation.

The inflammasome is a cytosolic protein complex that activates inflammatory responses. Inflammasome activation generally initiates other inflammatory signaling cascades. An inflammasome inhibitor could potentially quiesce a number of different inflammation pathways and even prevent the initiation of inflammation. Pharmaceuticals that target inflammasomes are in clinical development (see, for example, Marchetti et al., "OLT1177, a β-sulfonyl nitrile compound, safe in humans, inhibits the NLRP3 inflammasome and reverses the metabolic cost of inflammation," Proc. Nat'l Acad. Sci. U.S.A. 2018; 115(7)). The identification of an inflammasome antagonist that displays efficacy at inhibiting multiple inflammatory signaling pathways nevertheless remains elusive.

Inflammation creates a tremendous global disease burden. Osteoarthritis, for example, affects 25 to 35 million people in the United States. Inflammatory responses in joint cartilage and bone partially leads to osteoarthritis, which results in chronic pain and disability that gradually worsens with age. Symptomatic osteoarthritis of the knee occurs in over ten percent of persons aged 60 and above, and knee osteoarthritis decreases mobility more than any other medical condition in seniors.

Current pharmaceutical interventions for osteoarthritis are limited to analgesics, NSAIDs, and intra-articular steroid injections, each of which presents limiting side effects. In light of the limited effectiveness of pharmaceutical interventions, chronic knee osteoarthritis often results in progressive disability that eventually requires total joint replacement. The increased prevalence of osteoarthritis of the knee in aging and obese populations suggests a growing clinical need for safe and effective pharmaceutical interventions to delay and potentially eliminate the need for orthopedic surgery.

Osteoarthritis affects other joints including joints of the hand, feet, and hip, which causes pain and disability that impairs quality of life. Smaller joints of the hands and feet are less amenable to intra-articular steroid injections, for example, because the trauma caused by a steroid injection typically outweighs its therapeutic effect and because osteoarthritis generally affects multiple joints of the hand and feet, which multiplies the number of injections necessary to treat the osteoarthritis and multiplies the associated trauma. The relative surface area and size of hand and foot joints nevertheless increases the efficacy of topical therapeutics relative to the knees and hips. Innovative topical treatments for inflammation generally and osteoarthritis specifically are nevertheless lacking.

Pain associated with inflammation can be treated directly with analgesics such as opiates, which generally target opioid receptors in the brain. Local analgesics include NSAIDs, capsaicin, and lidocaine, each of which can be administered topically. Capsaicin targets vanilloid receptors, and lidocaine targets voltage-gated sodium channels. Additionally, N-methyl-D-aspartate (NMDA) receptor antagonists are known to display analgesic effects, which antagonists include, for example, ketamine and nitrous oxide. NMDA receptor antagonists are not generally prescribed for long-term pain management or to treat pain associated with inflammation.

The NMDA receptor is a glutamate receptor and calcium ion channel. The binding of two glutamates to an NMDA receptor activates the calcium ion channel to increase calcium permeability. Antagonists such as ketamine and nitrous oxide block the calcium channel. NMDA receptor activation can contribute to the development and maintenance of chronic pain conditions by inducing sensitization of pain-sensing neurons, and the NMDA receptor therefore plays a role in synaptic plasticity and pain.

Glutamate, which functions as a neurotransmitter when binding NMDA receptors, is also an amino acid building block of proteins and a precursor and metabolite in numerous other biochemical pathways. Glutamate is notably the transamination product of the citric acid cycle intermediate alpha-ketoglutarate (AKG), and a number of different enzymes interconvert glutamate and AKG.

The citric acid cycle (which is also known as the Krebs cycle) is a series of enzymatic reactions that take place in the mitochondria and generate energy in the form of adenosine triphosphate (ATP). Briefly, beta-oxidation breaks down fatty acids to produce acetyl-CoA, which enters the citric acid cycle in the mitochondria to generate ATP. AKG is not directly formed from fatty acids. Fatty acids first undergo beta-oxidation to generate acetyl-CoA, which is then converted to AKG. The enzyme glutamate dehydrogenase can catalyze the conversion of glutamate into AKG and NADPH, which NADPH is involved in cellular processes such as fatty acid synthesis and antioxidant defense. Whether pharmacological manipulation of the citric acid cycle or its intermediates can affect NMDA receptor activation to produce therapeutic effects, for example, by modulating glutamate concentration, remains unknown.

SUMMARY

Various aspects of this disclosure relate to topical compositions that comprise a fatty acid and tryptophan. The fatty acid is provided as a free fatty acid, which is generally present in equilibrium with its carboxylate conjugate base. The fatty acid decanoic acid has the carboxylate conjugate base decanoate, for example, and decanoate is typically also present in compositions that comprise both decanoic acid and an aqueous phase. The tryptophan is provided as a free amino acid, which generally exists as a mixture of zwitterionic and neutral tautomers in compositions of that comprise an aqueous phase.

Topical compositions comprising a fatty acid can advantageously reduce inflammasome-mediated inflammation. Without limiting this disclosure or any patent claim that matures from this disclosure, fatty acids can bind to and inhibit intracellular inflammasomes, which can reduce interleukin-1 beta (IL-1beta) signaling and corresponding inflammation. Without limiting this disclosure or any patent claim that matures from this disclosure, fatty acids bind to the lipopolysaccharide (LPS)-binding sites on inflammasome caspase activation and recruitment domains (CARDs), which inhibits inflammasomes. Without limiting this disclosure or any patent claim that matures from this disclosure, fatty acids can also serve as a carbon source for the citric acid cycle, which can increase concentrations of the citric acid cycle intermediate alpha-ketoglutarate, which alpha-ketoglutarate improves nitrogen transport and displays antioxidant properties. Without limiting this disclosure or any patent claim that matures from this disclosure, fatty acids also bind a specific locus on the NACHT domain on the NLRP3 inflammasome that possesses ATPase activity to inhibit activation of the NLRP3 inflammasome. Inhibition of the NACHT domain locus, for example, with the small molecule MCC950 is known to inhibit activation of the NLRP3 inflammasome. Without limiting this disclosure or any patent claim that matures from this disclosure, fatty acids can also inhibit the NLRP3 inflammasome by binding its NACHT domain.

Regardless of their precise mechanism of action, the examples provided below suggest that (1) the fatty acid decanoic acid modulates human monocytes and/or macrophages to reduce IL-1beta signaling, and (2) decanoic acid independently modulates human osteoarthritic chondrocytes to promote their re-differentiation. Each of these effects has an independent, favorable impact on osteoarthritis. Similar medium chain free fatty acids are expected to display similar effects.

Topical compositions comprising tryptophan can advantageously also reduce inflammasome-mediated inflammation and pain. Without limiting this disclosure or any patent claim that matures from this disclosure, tryptophan can bind toll-like receptors such as toll-like receptor 7 (TLR7) to inhibit the production of pro-inflammatory cytokines including IL-1beta, which inhibition of IL-1beta production likely occurs through an inflammasome-mediated pathway. Regardless of the precise mechanism, tryptophan and related indols reduce IL-1beta as well as other inflammatory cytokines including tumor-necrosis factor (TNF) and interferon gamma (IFNgamma), at least in peripheral blood mononuclear cells.

This summary section sets forth a general overview of features of the inventions of this disclosure. Other features and scope of the inventions of this disclosure are set forth in the following detailed description, exemplification, and claims. Nothing in either the preceding summary, background, and field sections or the following brief description of the drawings, detailed description, and exemplification sections shall limit any patent claim that matures from this disclosure. Any such granted patent claim shall instead be construed according to the language of the claim itself.

BRIEF DESCRIPTION OF THE DRAWINGS

FIG. 2A depicts human chondrocyte spheroids that were incubated for four days without decanoic acid, which spheroids settled through a hyaluronic acid hydrogel to the bottom surface of a culture well. FIG. 2B depicts human chondrocyte spheroids that were incubated for four days with decanoic acid, which spheroids generated interconnected networks that suspended the spheroids in a hyaluronic acid hydrogel above the bottom surface of the culture well.

FIG. 3A depicts human chondrocyte spheroids that were incubated for 20 days without decanoic acid, which spheroids settled on the bottom surface of a culture well to establish a monolayer on the surface. FIG. 3B depicts human chondrocyte spheroids that were incubated for 20 days with decanoic acid, which spheroids display large spheroid development or condensation that may be representative of enhanced differentiation.

FIG. 5A depicts the viability of resting cells, and FIG. 5B depicts the viability of activated cells. Cells treated with 6 millimolar decanoic acid displayed a significant decrease in viability whereas no lower concentration of decanoic acid reduced cell viability relative to vehicle controls.

DETAILED DESCRIPTION

Figure 1:
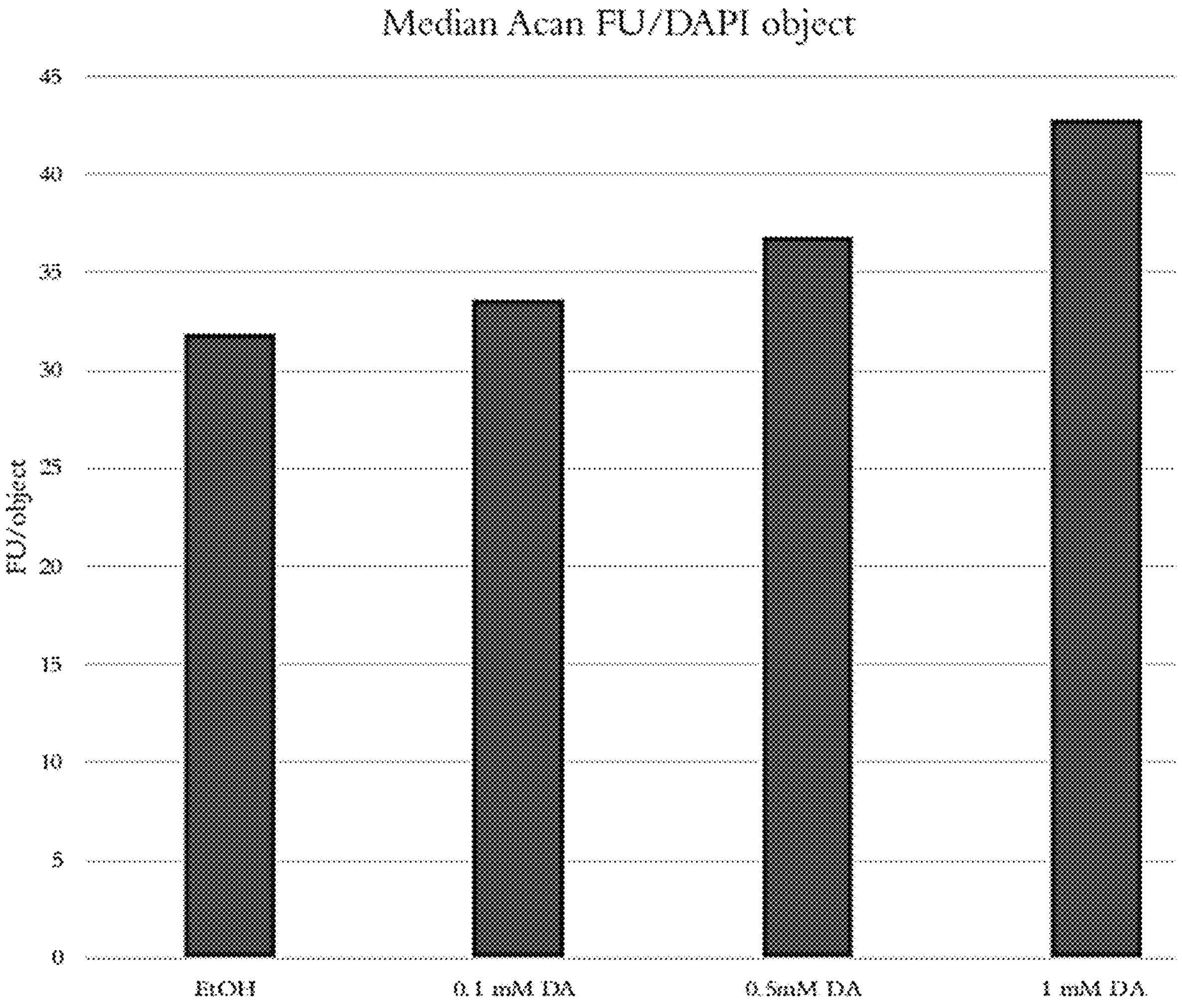
FIG. 1 is a bar graph that depicts increasing aggrecan (ACAN) immunostaining fluorescence (FU) of human osteoarthritic chondrocytes cultured with ethanol (EtOH) vehicle or increasing millimolar (mM) concentrations of decanoic acid (DA) relative to the 4',6-diamidino-2-phenylindole (DAPI) nuclear stain.

Various aspects of this disclosure relate to the discovery that the free fatty acid decanoic acid can both reduce the secretion of the pro-inflammatory cytokine IL-1beta from macrophages and increase re-differentiation of osteoarthritic chondrocytes to a normal phenotype. These findings suggest that free fatty acids generally and decanoic acid specifically have a beneficial effect on osteoarthritis. Various aspects of this disclosure relate to the discovery that tryptophan and its metabolites have favorable effects on inflammation (see, for example, Hajsl M, et al. "Tryptophan Metabolism, Inflammation, and Oxidative Stress in Patients with Neurovascular Disease." Metabolites 2020; 10:208; Stone TW & Williams RO. "Modulation of T cells by tryptophan metabolites in the kynurenine pathway." Trends in Pharmacological Sciences 2023; 44(7):442-56; Nayak BN & Buttar H. "Role of Tryptophan in Health and Disease." World Heart Journal 2019; 11(2):161-78). Based on these discoveries, topical, anti-inflammatory formulations were developed to partition both decanoic acid and tryptophan across the skin and into the underlying subcutaneous tissue and cartilage to treat osteoarthritis by reducing inflammation and pain and by promoting the re-differentiation of osteoarthritic chondrocytes.

The compositions of this disclosure generally comprise decanoic acid and tryptophan at concentrations of about 20 millimolar as well as propylene glycol, water, glycerin, and medium-chain triglycerides as solvents/cosolvents and penetration enhancers such as isopropyl myristate. The skilled practitioner will immediately appreciate that many variations upon the foregoing composition exist, and the following specification and claims disclose and encompass additional scope and features.

The compositions of this disclosure are generally useful to treat inflammation. This disclosure focuses upon inflammation associated with osteoarthritis. Many other conditions are treatable by reducing monocyte- and macrophage-mediated inflammation, and the compositions of this disclosure may also be useful for treating, for example, rheumatoid arthritis, polyarticular juvenile idiopathic arthritis, axial spondylarthritis, psoriatic arthritis, plaque psoriasis, lichen planus, acne vulgaris, dermatitis, Dupuytren's contracture, frozen shoulder, pre- and post-skin cosmetic procedures, peripheral neuropathy, diabetic peripheral neuropathy, chemotherapy-induced peripheral neuropathy (CIPN), shingles, and herpes simplex lesions among other conditions.

Various aspects of this disclosure relate to a composition, comprising a fatty acid and tryptophan. In some embodiments, the composition is formulated for topical administration to skin. In some specific embodiments, the composition is a topical, anti-inflammatory composition. In some specific embodiments, the composition is a topical, analgesic composition.

Various aspects of this disclosure relate to a composition, comprising chemical species that comprise a fatty acid, a carboxylate, and tryptophan. In some embodiments, the chemical species comprise water and one or more polyhydric alcohols (for example, glycerin and propylene glycol).

In some embodiments, the fatty acid is a saturated fatty acid. In some specific embodiments, the fatty acid is a saturated fatty acid comprising at least 6 and up to 14 carbon atoms. In some even more specific embodiments, the fatty acid is hexanoic acid, octanoic acid, decanoic acid, dodecanoic acid, tetradecanoic acid, or hexadecanoic acid. In some very specific embodiments, the fatty acid is decanoic acid.

In some embodiments, the fatty acid has a conjugate base, which is the carboxylate. In some embodiments, the composition comprises a carboxylate, wherein the carboxylate is the conjugate base of the fatty acid. In some embodiments, the fatty acid comprises a conjugate base, which is a carboxylate, and the composition comprises the carboxylate. Decanoic acid, for example, has a pKa (negative log of its acid dissociation constant) of about 4.9, which means that aqueous phases that comprise decanoic acid generally also include its conjugate base decanoate, at least at neutral pH. Various compositions of this disclosure comprise water, and a portion of decanoic acid that dissolves in the water will be deprotonated to form dissolved decanoate. The solubility of decanoic acid in water is about 150 parts per million by mass, and the compositions of this disclosure generally feature concentrations of decanoic acid that are greater than its solubility in water. The concentration of decanoate in the various compositions of this disclosure is therefore less than the concentration that might be determined based on pKa alone.

In some embodiments, the composition comprises a combined concentration of the fatty acid and the carboxylate of at least 300 parts per million and up to 3 percent by mass. In some specific embodiments, the composition comprises a combined concentration of the fatty acid and the carboxylate of at least 1,000 parts per million and up to 1.5 percent by mass. In some even more specific embodiments, the composition comprises a combined concentration of the fatty acid and the carboxylate of at least 1,133 parts per million and up to 1.02 percent by mass. In some very specific embodiments, the composition comprises a combined concentration of the fatty acid and the carboxylate of at least 1,700 parts per million and up to 6,800 parts per million by mass. Lower combined concentrations of a fatty acid and carboxylate display lower efficacy, and higher combined concentrations risk toxicity, which concentration-dependent effects are apparent in light of the exemplification section below and, for example, in FIGS. 4, 5A, and 5B. The therapeutic window for fatty acid concentration is therefore somewhat narrow.

In some embodiments, the tryptophan exists as zwitterionic and neutral tautomers. In this disclosure, the term "tryptophan" includes both zwitterionic and neutral tautomers of tryptophan and both enantiomers of tryptophan.

In some embodiments, the composition comprises one or both of L-tryptophan and D-tryptophan. In some specific embodiments, the composition comprises a racemic mixture of L- and D-tryptophan. In some specific embodiments, the composition comprises L-tryptophan, and the composition lacks D-tryptophan.

In some embodiments, the composition comprises tryptophan at a concentration of at least 2,700 parts per million and up to 10 percent by mass. In some specific embodiments, the composition comprises tryptophan at a concentration of at least 6,000 parts per million and up to 8 percent by mass. In some even more specific embodiments, the composition comprises tryptophan at a concentration of at least 9,000 parts per million and up to 8.1 percent by mass. In some very specific embodiments, the composition comprises tryptophan at a concentration of at least 1.3 percent and up to 5.4 percent by mass.

In some embodiments, the composition comprises water. In some specific embodiments, the composition comprises water at a concentration of at least 10 percent and up to 50 percent by mass. In some even more specific embodiments, the composition comprises water at a concentration of at least 19 percent and up to 39 percent by mass. In some very specific embodiments, the composition comprises water at a concentration of at least 24 percent and up to 34 percent by mass.

In some embodiments, the composition comprises the water at a greater concentration by mole than any other chemical species that is present in the composition. In some specific embodiments, the composition comprises each of the chemical species at a concentration by mole; the composition comprises the water at a greater concentration by mole than any other chemical species that is present in the composition; and the composition comprises the one or more alcohols at a combined concentration by mole, which is less than the concentration by mole of the water in the composition.

In some embodiments, the composition comprises one or more alcohols. The one or more alcohols assist with solubilizing the fatty acid and the tryptophan. The one or more alcohols also inhibit the vaporization of water from the composition.

In some embodiments, the composition comprises the fatty acid at a concentration that is greater than the solubility of the fatty acid in water. In some specific embodiments, the fatty acid has a solubility in water, and the composition comprises the fatty acid at a concentration that is greater than the solubility of the fatty acid in water.

In some embodiments, the composition comprises the tryptophan at a concentration that is greater than the solubility of the tryptophan in water. In some specific embodiments, the tryptophan has a solubility in water, and the composition comprises the tryptophan at a concentration that is greater than the solubility of the tryptophan in water.

In some embodiments, the composition comprises the one or more alcohols at a concentration of at least 30 percent and up to 70 percent by mass. In some specific embodiments, the composition comprises the one or more alcohols at a concentration of at least 40 percent and up to 60 percent by mass. In some very specific embodiments, the composition comprises the one or more alcohols at a concentration of at least 45 percent and up to 55 percent by mass.

In some embodiments, the one or more alcohols comprise one or more polyhydric alcohols. In some specific embodiments, the one or more alcohols consist of one or more polyhydric alcohols.

In some embodiments, the one or more alcohols comprise propylene glycol and glycerin. In some specific embodiments, the one or more alcohols consist of propylene glycol and glycerin.

In some embodiments, the composition comprises glycerin. In some specific embodiments, the composition comprises glycerin at a concentration of at least 10 percent and up to 40 percent by mass. In some even more specific embodiments, the composition comprises glycerin at a concentration of at least 12.6 percent and up to 37.2 percent by mass. In some very specific embodiments, the composition comprises glycerin at a concentration of at least 17.6 percent and up to 32.2 percent by mass.

In some embodiments, the composition comprises propylene glycol. In some specific embodiments, the composition comprises propylene glycol at a concentration of at least 15 percent and up to 60 percent by mass. In some even more specific embodiments, the composition comprises propylene glycol at a concentration of at least 20.8 percent and up to 41.6 percent by mass. In some very specific embodiments, the composition comprises propylene glycol at a concentration of at least 25.8 percent and up to 36.6 percent by mass.

In some embodiments, the composition comprises hydrogen phosphate and dihydrogen phosphate. Hydrogen phosphate and dihydrogen phosphate buffer the pH of the composition, which stabilizes various chemical species of the composition. When hydrogen phosphate and dihydrogen phosphate are present in a composition, then the hydrogen phosphate and dihydrogen phosphate are chemical species of the composition.

In some embodiments, the composition comprises hydrogen phosphate and dihydrogen phosphate at a combined concentration of at least 32 parts per million and up to 3,200 parts per million by mass. In some specific embodiments, the composition comprises the hydrogen phosphate and the dihydrogen phosphate at a combined concentration of at least 64 parts per million and up to 1,600 parts per million by mass. In some very specific embodiments, the composition comprises the hydrogen phosphate and the dihydrogen phosphate at a combined concentration of at least 160 parts per million and up to 640 parts per million by mass.

In some embodiments, the composition comprises a molar ratio of hydrogen phosphate and dihydrogen phosphate of at least 1:20 and up to 40:1 (hydrogen phosphate:dihydrogen phosphate). In some very specific embodiments, the composition comprises a molar ratio of hydrogen phosphate and dihydrogen phosphate of at least 1:10 and up to 20:1. In some very specific embodiments, the composition comprises a molar ratio of hydrogen phosphate and dihydrogen phosphate of at least 1:5 and up to 10:1.

In some embodiments, the composition comprises one or more of sodium cation, potassium cation, and chloride anion. In some specific embodiments, the composition comprises each of sodium cation, potassium cation, and chloride anion. When sodium cation, potassium cation, and/or chloride anion are present in a composition, then the sodium cation, potassium cation, and/or chloride anion are chemical species of the composition.

In some embodiments, the composition comprises SEPINEO® P 600, which consists of acrylamide/sodium acryloyldimethyltaurate copolymer, isohexadecane (CAS 297-628-2), and polyoxyethylene (20) sorbitan monooleate. The precise mixture of SEPINEO® P 600 is proprietary, but its safety data sheet indicates that it contains isohexadecane at a concentration of 20 to 40 percent. SEPINEO® P 600 and its components are included in various compositions of this disclosure as one or more of an emulsifier, stabilizer, and thickener.

Acrylamide/sodium acryloyldimethyltaurate copolymer exists in compositions of this disclosure as an anionic acrylamide/acryloyldimethyltaurate copolymer that undergoes ionic interactions with sodium cation and other cations of the compositions (for example, potassium cation) as well as hydrogen-bonding interactions with water and/or alcohol (s) of the compositions. At any specific instant, a single anionic acrylamide/acryloyldimethyltaurate copolymer chemical species may simultaneously interact with multiple different cations, water molecules, and alcohols through different non-covalent bonds with its many sulfonate groups. In this disclosure "acrylamide/acryloyldimethyltaurate copolymer" encompasses anionic acrylamide/acryloyldimethyltaurate copolymer in the presence or absence of one or more interactions with one or more other chemical species of a composition.

In some embodiments, the composition comprises acrylamide/acryloyldimethyltaurate copolymer. In some specific embodiments, the composition comprises acrylamide/acryloyldimethyltaurate copolymer at a concentration of at least 1,000 parts per million and up to 10 percent by mass. In some even more specific embodiments, the composition comprises acrylamide/acryloyldimethyltaurate copolymer at a concentration of at least 2,000 parts per million and up to 6 percent by mass. In some very specific embodiments, the composition comprises acrylamide/acryloyldimethyltaurate copolymer at a concentration of at least 4,000 parts per million and up to 4 percent by mass. When acrylamide/acryloyldimethyltaurate copolymer is present in a composition, then the acrylamide/acryloyldimethyltaurate copolymer is a chemical species of the composition.

In some embodiments, the composition comprises a branched alkane. In some specific embodiments, the composition comprises the branched alkane at a concentration of at least 1,000 parts per million and up to 10 percent by mass. In some even more specific embodiments, the composition comprises the branched alkane at a concentration of at least 2,000 parts per million and up to 6 percent by mass. In some very specific embodiments, the composition comprises the branched alkane at a concentration of at least 4,000 parts per million and up to 4 percent by mass. In this specification, branched alkanes are saturated hydrocarbon chains that comprise 10 to 22 total carbon atoms ant that comprise at least one tertiary or quaternary carbon atom. Branched alkanes include, for example, isohexadecane. When the branched alkane is present in a composition, then the branched alkane is a chemical species of the composition. Branched alkanes serve as penetration enhancers to facilitate partitioning of the fatty acid from the composition across the skin and into the underlying subcutaneous tissue and cartilage.

In some embodiments, the composition comprises isohexadecane. In some specific embodiments, the composition comprises isohexadecane at a concentration of at least 1,000 parts per million and up to 10 percent by mass. In some even more specific embodiments, the composition comprises isohexadecane at a concentration of at least 2,000 parts per million and up to 6 percent by mass. In some very specific embodiments, the composition comprises isohexadecane at a concentration of at least 4,000 parts per million and up to 4 percent by mass. When isohexadecane is present in a composition, then the isohexadecane is a chemical species of the composition.

In some embodiments, the composition comprises a polysorbate. In some specific embodiments, the composition comprises the polysorbate at a concentration of at least 1,000 parts per million and up to 10 percent by mass. In some even more specific embodiments, the composition comprises the polysorbate at a concentration of at least 2,000 parts per million and up to 6 percent by mass. In some very specific embodiments, the composition comprises the polysorbate at a concentration of at least 4,000 parts per million and up to 4 percent by mass. Polysorbates include polyoxyethylene (20) sorbitan monolaurate, polyoxyethylene (20) sorbitan monopalmitate, polyoxyethylene (20) sorbitan monostearate, and polyoxyethylene (20) sorbitan monooleate, which are generally useful as emulsifiers. When the polysorbate is present in a composition, then the polysorbate is a chemical species of the composition.

In some embodiments, the composition comprises polyoxyethylene (20) sorbitan monooleate. In some specific embodiments, the composition comprises polyoxyethylene (20) sorbitan monooleate at a concentration of at least 1,000 parts per million and up to 10 percent by mass. In some even more specific embodiments, the composition comprises polyoxyethylene (20) sorbitan monooleate at a concentration of at least 2,000 parts per million and up to 6 percent by mass. In some very specific embodiments, the composition comprises polyoxyethylene (20) sorbitan monooleate at a concentration of at least 4,000 parts per million and up to 4 percent by mass. When polyoxyethylene (20) sorbitan monooleate is present in a composition, then the polyoxyethylene (20) sorbitan monooleate is a chemical species of the composition.

In some embodiments, the composition comprises triglycerides. In some specific embodiments, the composition comprises medium-chain triglycerides. Triglycerides are a solvent for the fatty acid, and they also serve as a penetration enhancer to facilitate partitioning of the fatty acid from the composition across the skin and into the underlying subcutaneous tissue and cartilage.

In some embodiments, the composition comprises triglycerides at a concentration of at least 2 percent and up to 25 percent by mass. In some specific embodiments, the composition comprises triglycerides at a concentration of at least 2.7 and up to 24 percent by mass. In some very specific embodiments, the composition comprises triglycerides at a concentration of at least 4.2 percent and up to 17 percent by mass.

In some embodiments, the triglycerides comprise esters of saturated fatty acids. In some specific embodiments, the triglycerides comprise esters of saturated fatty acids comprising at least 6 and up to 14 total carbon atoms. In some even more specific embodiments, the triglycerides comprise esters of one or more of hexanoic acid, octanoic acid, decanoic acid, dodecanoic acid, tetradecanoic acid, and hexadecanoic acid. In some very specific embodiments, the triglycerides comprise esters of one or both of octanoic acid and decanoic acid.

In some embodiments, the triglycerides comprise esters of octanoic acid at a concentration of at least 50 percent and up to 80 percent by mass and esters of decanoic acid at a concentration of at least 20 percent and up to 50 percent by mass. In some specific embodiments, the triglycerides comprise esters of octanoic acid at a concentration of at least 50 percent and up to 80 percent by mass and esters of decanoic acid at a concentration of at least 20 percent and up to 50 percent by mass, and the triglycerides lack any other esters.

In some embodiments, the composition comprises an emollient. In some specific embodiments, the emollient comprises a saturated hydrocarbon chain comprising at least 10 and up to 22 total carbon atoms. In some very specific embodiments, the emollient is isopropyl myristate or isopropyl palmitate. Emollients that comprise a saturated hydrocarbon chain serve as penetration enhancers to facilitate partitioning of the fatty acid from the composition across the skin and into the underlying subcutaneous tissue and cartilage.

In some embodiments, the composition comprises the emollient at a concentration of at least 6,500 parts per million and up to 10 percent by mass. In some specific embodiments, the composition comprises the emollient at a concentration of at least 1 percent and up to 8 percent by mass. In some very specific embodiments, the composition comprises the emollient at a concentration of at least 1.9 percent and up to 7.6 percent by mass.

In some embodiments, the composition comprises a metal oxide. In some specific embodiments, the composition comprises titanium dioxide or zinc oxide. In some very specific embodiments, the composition comprises titanium dioxide. Metal oxides are used to color compositions of the disclosure, for example, to assist users in identifying that a composition has been uniformly spread over the skin. Such identification is useful, for example, to assess whether an effective amount of the composition has been applied to the skin.

In some embodiments, the composition comprises the metal oxide at a concentration of at least 2,000 parts per million and up to 4 percent by mass. In some specific embodiments, the composition comprises the metal oxide at a concentration of at least 4,000 parts per million and up to 3 percent by mass. In some very specific embodiments, the composition comprises the metal oxide at a concentration of at least 6,000 parts per million and up to 2 percent by mass.

In some embodiments, the composition comprises one or more additional free amino acids. In some specific embodiments, the composition comprises one or more free additional amino acids selected from cysteine, methionine, glutamate, lysine, arginine, histidine, and tyrosine. Compositions of this disclosure optionally comprise free amino acids selected from one or more of cysteine, methionine, lysine, arginine, histidine, and tyrosine at concentrations at which the one or more free amino acids display antioxidant properties. Compositions of this disclosure optionally comprise glutamate at a concentration at which the glutamate displays one or both of anti-inflammatory and analgesic properties. In this disclosure, the term "cysteine" includes zwitterionic and neutral tautomers of cysteine and thiols of the foregoing. In this disclosure, the term "methionine" includes zwitterionic and neutral tautomers of methionine. In this disclosure, the term "glutamate" includes zwitterionic and neutral tautomers of glutamate. In this disclosure, the term "lysine" includes zwitterionic and neutral tautomers of lysine and aminium ions of the foregoing. In this disclosure, the term "arginine" includes zwitterionic and neutral tautomers of arginine and guanidinium ions of the foregoing. In this disclosure, the term "histidine" includes zwitterionic and neutral tautomers of histidine and imidazolium ions of the foregoing. In this disclosure, the term "tyrosine" includes zwitterionic and neutral tautomers of tyrosine.

In some embodiments, the composition comprises cysteine at a concentration of at least 1,000 parts per million and up to 2 percent by mass. In some specific embodiments, the composition comprises cysteine at a concentration of at least 2,000 parts per million and up to 1 percent by mass. In some very specific embodiments, the composition comprises cysteine at a concentration of at least 3,000 parts per million and up to 7,000 parts per million by mass.

In some embodiments, the composition comprises methionine at a concentration of at least 1,000 parts per million and up to 2 percent by mass. In some specific embodiments, the composition comprises methionine at a concentration of at least 2,000 parts per million and up to 1 percent by mass. In some very specific embodiments, the composition comprises methionine at a concentration of at least 3,000 parts per million and up to 7,000 parts per million by mass.

In some embodiments, the composition comprises lysine at a concentration of at least 1,000 parts per million and up to 2 percent by mass. In some specific embodiments, the composition comprises lysine at a concentration of at least 2,000 parts per million and up to 1 percent by mass. In some very specific embodiments, the composition comprises lysine at a concentration of at least 3,000 parts per million and up to 7,000 parts per million by mass.

In some embodiments, the composition comprises arginine at a concentration of at least 1,000 parts per million and up to 2 percent by mass. In some specific embodiments, the composition comprises arginine at a concentration of at least 2,000 parts per million and up to 1 percent by mass. In some very specific embodiments, the composition comprises arginine at a concentration of at least 3,000 parts per million and up to 7,000 parts per million by mass.

In some embodiments, the composition comprises histidine at a concentration of at least 1,000 parts per million and up to 2 percent by mass. In some specific embodiments, the composition comprises histidine at a concentration of at least 2,000 parts per million and up to 1 percent by mass. In some very specific embodiments, the composition comprises histidine at a concentration of at least 3,000 parts per million and up to 7,000 parts per million by mass.

In some embodiments, the composition comprises tyrosine at a concentration of at least 1,000 parts per million and up to 2 percent by mass. In some specific embodiments, the composition comprises tyrosine at a concentration of at least 2,000 parts per million and up to 1 percent by mass. In some very specific embodiments, the composition comprises tyrosine at a concentration of at least 3,000 parts per million and up to 7,000 parts per million by mass.

In some embodiments, the composition comprises glutamate at a concentration of at least 290 parts per million and up to 2.9 percent by mass. In some specific embodiments, the composition comprises glutamate at a concentration of at least 580 parts per million and up to 1.45 percent by mass. In some very specific embodiments, the composition comprises glutamate at a concentration of at least 967 parts per million and up to 8,700 parts per million by mass.

In some embodiments, the fatty acid is hexanoic acid, and the carboxylate is hexanoate.

In some embodiments, the fatty acid is octanoic acid, and the carboxylate is octanoate.

In some embodiments, the fatty acid is decanoic acid, and the carboxylate is decanoate.

In some embodiments, the fatty acid is dodecanoic acid, and the carboxylate is dodecanoate.

In some embodiments, the fatty acid is tetradecanoic acid, and the carboxylate is tetradecanoate.

In some embodiments, the fatty acid is hexadecanoic acid, and the carboxylate is hexadecanoate.

In some embodiments, the composition comprises decanoic acid and decanoate at a combined concentration of at least 1,133 parts per million and up to 1.02 percent by mass; tryptophan at a concentration of at least 9,000 parts per million and up to 8.1 percent by mass; glycerin at a concentration of at least 12.6 percent and up to 37.2 percent by mass; propylene glycol at a concentration of at least 20.8 percent and up to 41.6 percent by mass; triglycerides at a concentration of at least 2.7 and up to 24 percent by mass; and water at a concentration of at least 19 percent and up to 39 percent by mass. In some specific embodiments, the composition comprises decanoic acid and decanoate at a combined concentration of at least 1,700 parts per million and up to 6,800 parts per million by mass; tryptophan at a concentration of at least 1.3 percent and up to 5.4 percent by mass; glycerin at a concentration of at least 17.6 percent and up to 32.2 percent by mass; propylene glycol at a concentration of at least 25.8 percent and up to 36.6 percent by mass; triglycerides at a concentration of at least 4.2 percent and up to 17 percent by mass; and water at a concentration of at least 24 percent and up to 34 percent by mass. In some very specific embodiments, the composition comprises decanoic acid and decanoate at a combined concentration of at least 3,000 parts per million and up to 3,800 parts per million by mass; tryptophan at a concentration of at least 2.2 percent and up to 3.4 percent by mass; glycerin at a concentration of at least 18 percent and up to 28 percent by mass; propylene glycol at a concentration of at least 28 percent and up to 34 percent by mass; triglycerides at a concentration of at least 6.5 percent and up to 10.5 percent by mass; and water at a concentration of at least 26 percent and up to 32 percent by mass.

In some embodiments, the composition is formulated for topical, transdermal, transmucosal, or intralesional administration. In some specific embodiments, the composition is formulated for topical administration.

In some embodiments, the composition is an emulsified cream, lotion, or ointment. When the composition is an emulsified cream, lotion, or ointment, then the composition typically comprises water, for example, at a concentration of at least 10 percent and up to 50 percent by mass. When the composition is an emulsified cream, lotion, or ointment, then the composition typically comprises propylene glycol, for example, at a concentration of at least 15 percent and up to 60 percent by mass. When the composition is an emulsified cream, lotion, or ointment, then the composition typically comprises glycerin, for example, at a concentration of at least 10 percent and up to 40 percent by mass.

In some embodiments, the composition is a tablet, powder, or granulate. In some specific embodiments, the composition is an effervescent tablet. When the composition is a tablet, powder, or granulate, then the composition typically lacks water at a concentration greater than 5 percent. When the composition is a tablet, powder, or granulate, then the composition typically lacks propylene glycol at a concentration greater than 5 percent. When the composition is a tablet, powder, or granulate, then the composition typically lacks glycerin at a concentration greater than 5 percent. When the composition is an effervescent composition (for example, an effervescent tablet, an effervescent powder, or an effervescent granulate), then the composition typically comprises one or more bicarbonate salts, such as sodium bicarbonate or magnesium bicarbonate, and the composition typically comprises one or more Brønsted acids, such as citric acid, which one or more bicarbonate salts and one or more Brønsted acids are typically present in the composition in a solid format, and which one or more bicarbonate salts and one or more Brønsted acids are typically present in sufficient molar concentrations to convert at least a portion of the bicarbonate into carbon dioxide when the composition is dispersed in water. While the fatty acids of this disclosure are Brønsted acids, an effervescent composition of this disclosure generally comprises one or more Brønsted acids in addition to the fatty acid because fatty acids and their conjugate bases generally lack sufficient solubility in water to deprotonate a significant portion of the bicarbonate of an effervescent composition.

Various aspects of this disclosure relate to a method of administering an anti-inflammatory to a subject, comprising dispersing the composition in water to produce a treatment composition and soaking at least a portion of the body of the subject in the treatment composition to administer the composition. In such embodiments, the anti-inflammatory composition is typically a tablet, such as an effervescent tablet, or a powder or granulate. The portion of the body is typically targeted by the treatment, for example, because the subject presents with a health condition or symptom thereof that affects the portion of the body, which body portion may include, for example, one or both feet, one or both lower legs, one or both legs, one or both hands, one or both arms, and/or the torso of the subject. A subject who presents with peripheral neuropathy that is localized to the feet, for example, may administer the anti-inflammatory composition by soaking his or her feet in the treatment composition. A subject who presents with chemotherapy-induced peripheral neuropathy (CIPN), for example, may administer the anti-inflammatory composition by dispersing the anti-inflammatory composition in a bath and by soaking his or her body in the bath. A subject who presents with plaque psoriasis patches that cover various different regions of the body, for example, may administer the anti-inflammatory composition by dispersing the anti-inflammatory composition in a bath and by soaking his or her body in the bath.

Various aspects of this disclosure relate to a method to treat skin of a subject, comprising providing a composition as described anywhere in this disclosure and administering an effective amount of the composition to skin of the subject.

Various aspects of this disclosure relate to a method to treat pain or inflammation in a subject, comprising providing a composition as described anywhere in this disclosure and administering an effective amount of the composition to skin of the subject.

In this specification, "treat" refers to at least one of: to cure a health condition; to increase the probability that a health condition will be cured; to shorten the time over which a health condition is cured; to increase the probability that the time necessary to cure a health condition will be shortened; to decrease the severity of a health condition; to increase the probability that the severity of a health condition will decrease; to shorten the time over which the severity of a health condition is decreased; to increase the probability that the time necessary to decrease the severity of a health condition will be shortened; to inhibit a health condition from worsening; to increase the probability that a health condition will not worsen; to delay the worsening of a health condition; to increase the probability that the worsening of a health condition will be delayed; to inhibit the occurrence or recurrence of a health condition; to decrease the probability that a health condition will occur or reoccur; to delay the onset of a health condition; to increase the probability that the onset of a health condition will be delayed; to alleviate at least one symptom of a health condition; to increase the probability that at least one symptom of a health condition will be alleviated; to shorten the time over which at least one symptom of a health condition is alleviated; to increase the probability that the time necessary to alleviate at least one symptom of a health condition will be shortened; to decrease the severity of at least one symptom of a health condition; to increase the probability that the severity of at least one symptom of a health condition will be decreased; to shorten the time over which the severity of at least one symptom of a health condition is decreased; to increase the probability that the time necessary to decrease the severity of at least one symptom of a health condition will be shortened; to inhibit at least one symptom of a health condition from worsening; to increase the probability that at least one symptom of a health condition will not worsen; to delay the worsening of at least one symptom of a health condition; to increase the probability that the worsening of at least one symptom of a health condition will be delayed; to inhibit at least one symptom of a health condition from occurring or reoccurring; to decrease the probability that at least one symptom of a health condition will occur or reoccur; to delay the onset of at least one symptom of a health condition; and to increase the probability that the onset of at least one symptom of a health condition will be delayed.

Various aspects of this disclosure relate to a method to treat osteoarthritis in a subject, comprising providing a composition as described anywhere in this disclosure and administering an effective amount of the composition to skin of the subject.

Various aspects of this disclosure relate to a method to inhibit inflammasome-mediated signaling in a subject, comprising providing a composition as described anywhere in this disclosure and administering an effective amount of the composition to skin of the subject.

Various aspects of this disclosure relate to a method to reduce IL-1beta in a subject, comprising providing a composition as described anywhere in this disclosure and administering an effective amount of the composition to skin of the subject.

Various aspects of this disclosure relate to a method to promote chondrocyte re-differentiation in a subject, comprising providing a composition as described anywhere in this disclosure and administering an effective amount of the composition to skin of the subject.

In some embodiments, the subject is a mammal. In some specific embodiments, the subject is a rodent, lagomorph, feline, canine, porcine, ovine, caprine, *lama*, bovine, equine, or primate. In some even more specific embodiments, the subject is a human. In some very specific embodiments, the subject is a human who presents with osteoarthritis.

In some embodiments, the subject presents with osteoarthritis, rheumatoid arthritis, polyarticular juvenile idiopathic arthritis, axial spondylarthritis, psoriatic arthritis, plaque psoriasis, hidradenitis suppurativa, lichen planus, acne vulgaris, dermatitis, Dupuytren's contracture, and frozen shoulder among other conditions. In some specific embodiments, the subject presents with osteoarthritis In some embodiments, the effective amount is about 50 milligrams to about 10 grams of the composition. In some specific embodiments, the effective amount is about 100 milligrams to about 5 grams of the composition. In some very specific embodiments, the effective amount is about 200 milligrams to about 2.5 grams of the composition.

In some embodiments, the administering is topical administering.

In some embodiments, the composition is formulated such that the fatty acid partitions through the skin into one or both of subcutaneous tissue and cartilage following the administering. In some specific embodiments, the effective amount is effective to partition the fatty acid through the skin into one or both of subcutaneous tissue and cartilage.

In some embodiments, the composition is formulated to convert at least a portion of the carboxylate into the fatty acid following the administering to produce a converted fatty acid. In some specific embodiments, the administering converts the portion of the carboxylate into the converted fatty acid. In some very specific embodiments, the administering converts the portion of the carboxylate into the converted fatty acid, and the administering partitions the converted fatty acid through the skin one or both of subcutaneous tissue and cartilage.

In some embodiments, the composition is formulated such that the tryptophan partitions through the skin into one or both of subcutaneous tissue and cartilage following the administering. In some specific embodiments, the effective amount is effective to partition the tryptophan through the skin into one or both of subcutaneous tissue and cartilage.

In some embodiments, the effective amount is effective to reduce inflammasome-mediated inflammation in one or both of subcutaneous tissue and cartilage following the administering. In some specific embodiments, the fatty acid reduces the inflammasome-mediated inflammation in one or both of subcutaneous tissue and cartilage following the administering. In some specific embodiments, the tryptophan reduces the inflammasome-mediated inflammation in one or both of subcutaneous tissue and cartilage following the administering. In some very specific embodiments, the tryptophan and the fatty acid synergistically reduce the inflammasome-mediated inflammation in one or both of subcutaneous tissue and cartilage following the administering.

In some embodiments, the fatty acid reduces inflammasome-mediated inflammation by binding to an inflammasome within a cell. In some specific embodiments, the fatty acid reduces the inflammasome-mediated inflammation by binding to an LPS-binding site on an inflammasome within a cell. In some very specific embodiments, the fatty acid reduces the inflammasome-mediated inflammation by binding to an LPS-binding site on a CARD domain.

In some embodiments, the fatty acid reduces inflammasome-mediated inflammation by binding to an inflammasome within a leukocyte. In some specific embodiments, the fatty acid reduces the inflammasome-mediated inflammation by binding to an inflammasome within a monocyte or macrophage.

In some embodiments, the composition reduces inflammasome-mediated inflammation. In some specific embodiments, the composition treats inflammation by reducing inflammasome-mediated inflammation.

In some embodiments, the effective amount is effective to reduce the IL-1beta in one or both of subcutaneous tissue and cartilage following the administering. In some specific embodiments, the fatty acid reduces IL-1beta in one or both of subcutaneous tissue and cartilage following the administering. In some specific embodiments, the tryptophan reduces IL-1beta in one or both of subcutaneous tissue and cartilage following the administering. In some very specific embodiments, the tryptophan and the fatty acid synergistically reduce IL-1beta in one or both of subcutaneous tissue and cartilage following the administering.

In some embodiments, the effective amount is effective to inhibit GasDermin D in cells of one or both of the subcutaneous tissue and cartilage.

In some embodiments, the effective amount is effective to increase alpha-ketoglutarate concentration in chondrocytes of the cartilage. In some specific embodiments, the effective amount comprises a sufficient amount of the fatty acid to increase alpha-ketoglutarate concentration in chondrocytes of the cartilage.

In some embodiments, the effective amount is effective to increase transcription factor SOX9 expression in chondrocytes following the administering. In some specific embodiments, the effective amount comprises sufficient fatty acid to increase SOX9 expression in chondrocytes following the administering. In some specific embodiments, the effective amount comprises sufficient tryptophan to increase SOX9 expression in chondrocytes following the administering. In some very specific embodiments, the tryptophan and the fatty acid are synergistically effective to increase SOX9 expression in chondrocytes following the administering.

In some embodiments, the effective amount is effective to re-differentiate chondrocytes in one or both of subcutaneous tissue and cartilage following the administering. In some specific embodiments, the fatty acid re-differentiates chondrocytes in one or both of subcutaneous tissue and cartilage following the administering. In some specific embodiments, the tryptophan re-differentiates chondrocytes in one or both of subcutaneous tissue and cartilage following the administering. In some very specific embodiments, the tryptophan and the fatty acid synergistically re-differentiate chondrocytes in cartilage following the administering.

In some embodiments, the effective amount is effective to re-differentiate osteoarthritic chondrocytes in proximity to the skin to which the composition is topically administered. In some specific embodiments, the fatty acid re-differentiates osteoarthritic chondrocytes in proximity to the skin to which the composition is topically administered. In some specific embodiments, the tryptophan re-differentiates osteoarthritic chondrocytes in proximity to the skin to which the composition is topically administered. In some very specific embodiments, the tryptophan and the fatty acid synergistically re-differentiate osteoarthritic chondrocytes in proximity to the skin to which the composition is topically administered.

In some embodiments, the effective amount is effective to increase collagen, type II, alpha 1 (Col2a1) in one or both of subcutaneous tissue and cartilage following the administering. In some specific embodiments, the fatty acid increases Col2a1 in one or both of subcutaneous tissue and cartilage following the administering. In some specific embodiments, the tryptophan increases Col2a1 in one or both of subcutaneous tissue and cartilage following the administering. In some very specific embodiments, the tryptophan and the fatty acid synergistically increase Col2a1 in one or both of subcutaneous tissue and cartilage following the administering.

In some embodiments, the effective amount is effective to increase ACAN in one or both of subcutaneous tissue and cartilage following the administering. In some specific embodiments, the fatty acid increases ACAN in one or both of subcutaneous tissue and cartilage following the administering. In some specific embodiments, the tryptophan increases ACAN in one or both of subcutaneous tissue and cartilage following the administering. In some very specific embodiments, the tryptophan and the fatty acid synergistically increase ACAN in one or both of subcutaneous tissue and cartilage following the administering.

In some embodiments, the method comprises identifying a subject who presents with osteoarthritis or a symptom of osteoarthritis.

In some embodiments, the osteoarthritis or the symptom is localized to at least one region of the body of the subject, and the method comprises topically administering an effective amount of the composition to skin of the region, wherein the effective amount is effective to treat the osteoarthritis or the symptom that is localized to the region.

In some embodiments, the region of the body is a joint. In some specific embodiments, the joint is selected from a digit, ankle, knee, hip, wrist, elbow, or shoulder. In some very specific embodiments, the joint is a knee.

In some embodiments, the composition is not administered to the face.

In some embodiments, the composition is not administered to the hands.

In some embodiments, the composition is not administered to the torso.

In some embodiments, the composition is not administered to medial portions of the limbs that are distal to a joint.

In some embodiments, the composition is administered to a joint, and the composition is not administered to other portions of the body. In some specific embodiments, the composition is administered to an inflamed joint, and the composition is not administered to other portions of the body. In some very specific embodiments, the composition is administered to an osteoarthritic joint, and the composition is not administered to other portions of the body.

EXEMPLIFICATION

Example 1. The Fatty Acid Decanoic Acid Increases SOX9, ACAN, and Col2a1 Expression in Human Osteoarthritic Chondrocytes Human osteoarthritic chondrocytes were derived from osteoarthritic tissue and cultured for 24 days in the presence of decanoic acid with medium exchanges performed weekly. The chondrocytes were layered on top of a hyaluronic acid hydrogel (SYNVISC®, Sanofi-Aventis, United States) to promote a three-dimensional culture environment. Following 24 days, the cells were fixed with paraformaldehyde and immunostained for SOX9, Col2a1, and ACAN.

Exposure of high-density monolayers of osteoarthritic chondrocytes to decanoic acid enhanced nuclear staining for SOX9 in a dose-dependent manner for cultures comprising ethanol vehicle, 0.1 millimolar decanoic acid, 0.5 millimolar decanoic acid, and 1 millimolar decanoic acid. Cell cultures containing 1 millimolar decanoic acid appeared to exhibit enhanced spheroid development or condensation, and the resulting spheroids also stained strongly for SOX9. The correlation between decanoic acid concentration and SOX9 expression suggests that decanoic acid promotes chondrocyte redifferentiation.

Exposure of high-density monolayers of osteoarthritic chondrocytes to decanoic acid resulted in dose-dependent punctate staining for ACAN for cultures comprising ethanol vehicle, 0.1 millimolar decanoic acid, 0.5 millimolar decanoic acid, and 1 millimolar decanoic acid. Exposure of low-density monolayers of osteoarthritic chondrocytes to decanoic acid resulted in dose-dependent intracellular staining for ACAN with the strongest staining observed at 1 millimolar decanoic acid (FIG. 1). Chondrocyte spheroids exhibited strong ACAN immunostaining when exposed to 1 millimolar decanoic acid.

Exposure of high-density monolayers of osteoarthritic chondrocytes to decanoic acid resulted in dose-dependent punctate staining for Col2a1 for cultures comprising ethanol vehicle, 0.1 millimolar decanoic acid, 0.5 millimolar decanoic acid, and 1 millimolar decanoic acid with peak staining observed at 0.5 millimolar decanoic acid. Exposure of low-density monolayers of osteoarthritic chondrocytes to decanoic acid resulted in strong punctate immunostaining for Col2a1 for chondrocytes cultured with 1 millimolar decanoic acid.

The foregoing results suggest that decanoic acid is effective at re-differentiating osteoarthritic chondrocytes.

Example 2. The Fatty Acid Decanoic Acid Increases Col2a1 Expression in Human Osteoarthritic Chondrocytes and Promotes Distinct Spheroid Morphologies Human osteoarthritic chondrocytes were derived from osteoarthritic tissue and cultured for 20 days in the presence of decanoic acid with medium exchanges performed every 2-3 days. The chondrocytes were layered on top of a hyaluronic acid hydrogel (SYNVISC®, Sanofi-Aventis, United States) to promote a three-dimensional culture environment. Following 20 days, hyaluronidase was added to release the cells from the hydrogel, the cells were collected, and total RNA was isolated.

Quantitative, real-time reverse transcript-polymerase chain reaction (real-time RT-PCR) was performed with delta-delta CT analysis for relative gene expression against GAPDH, actin, and 18S ribosomal RNA transcripts. 0.5 millimolar decanoic acid resulted in a 1-fold increase in Col2a1 mRNA, and 1 millimolar decanoic acid resulted in a 7-fold increase in Col2a1 mRNA.

Figure 2A:
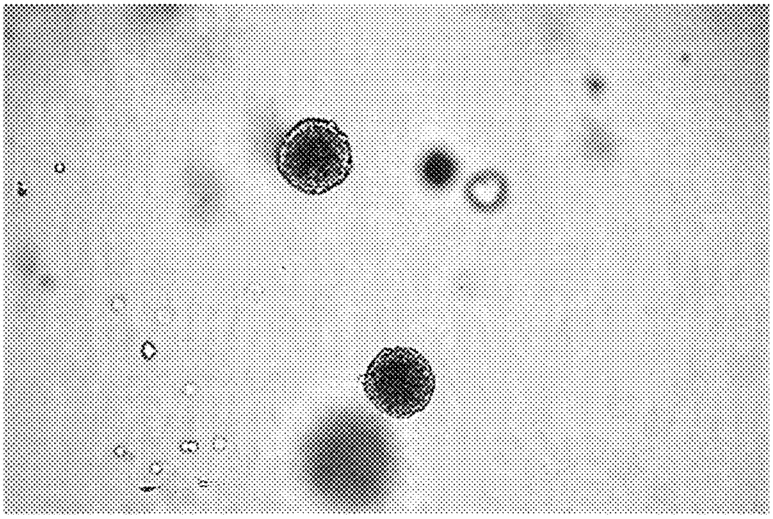
FIGS. 2A and 2B are microscope images of human chondrocyte spheroids following four days of incubation with and without decanoic acid.
Figure 2B:
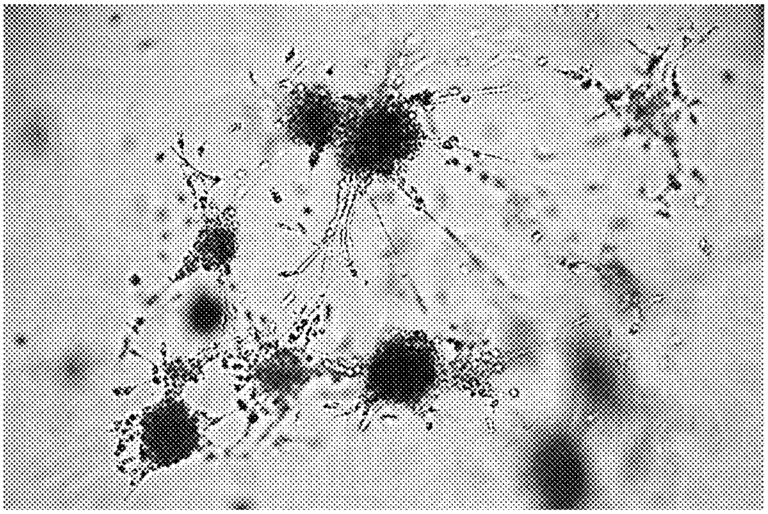

Examination of the chondrocyte spheroids after 4 days of culture revealed distinct morphological differences in the presence and absence of decanoic acid, which promoted interconnected networks of spheroids. The interconnected networks allowed the chondrocyte spheroids to exist suspended in the hyaluronic acid hydrogel in contrast with the absence of decanoic acid, in which case the spheroids drifted to the surface below the hydrogel (FIGS. 2A & 2B).

Figure 3A:
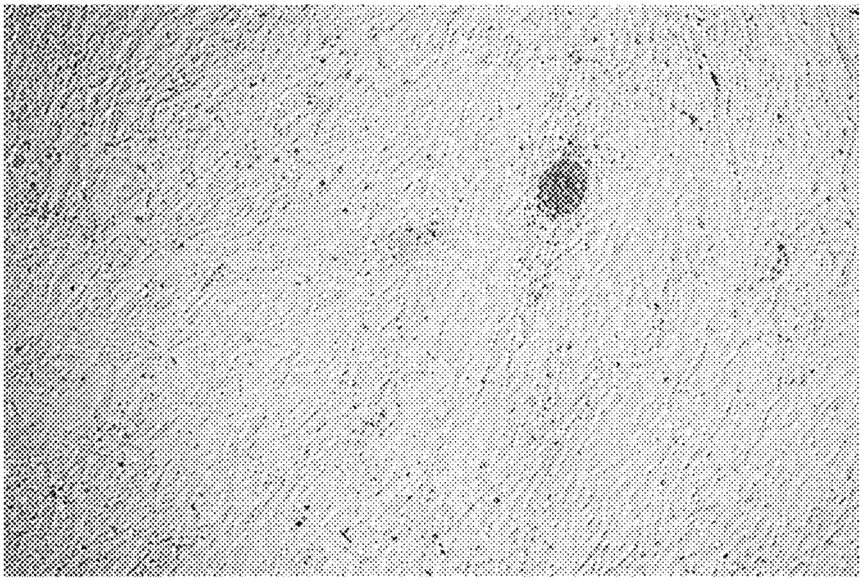
FIGS. 3A and 3B are microscope images of human chondrocyte spheroids following 20 days of incubation with and without decanoic acid.
Figure 3B:
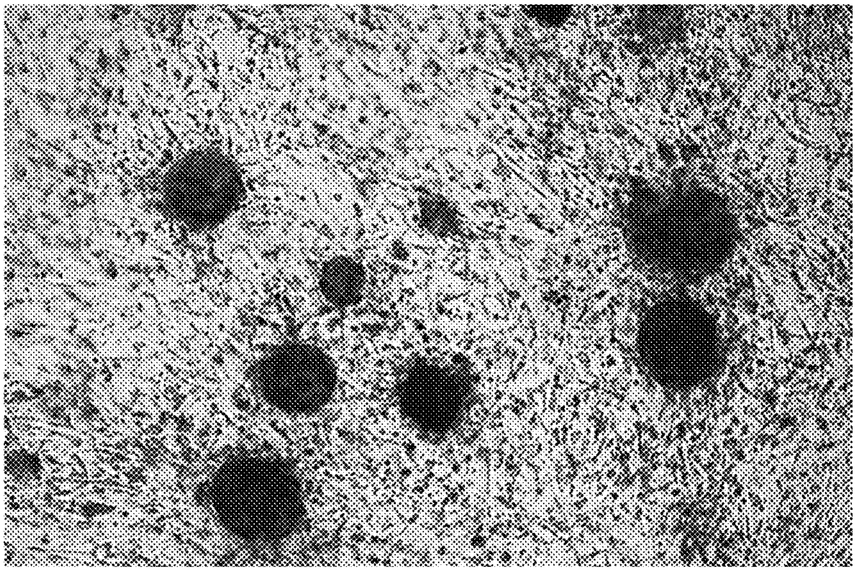

Examination of the chondrocyte spheroids after 20 days of culture revealed additional morphological differences in the presence and absence of decanoic acid. Control chondrocytes established a monolayer on the bottom surface of their culture wells (FIG. 3A). The addition of decanoic acid resulted in large spheroid development or condensation, which is indicative of enhanced differentiation (FIG. 3B).

The foregoing findings suggest that decanoic acid is effective at re-differentiating osteoarthritic chondrocytes.

Example 3. The Fatty Acid Decanoic Acid Inhibits IL-1Beta Release from Human Macrophage-Like Cells The human monocyte cell line THP-1 was differentiated into macrophage-like cells with PMA for 72 hours. Following differentiation, the cells were exposed to decanoic acid in 96-well tissue culture plates at 25,000 cells per well at decanoic acid concentrations ranging from 0.2 millimolar to 6 millimolar. Cells were then activated with 100 nanograms per milliliter LPS for 24 hours followed by an additional hour with 10 millimolar adenosine triphosphate (ATP). IL-1beta release was quantified by enzyme-linked immunosorbent assay (ELISA).

Figure 4:
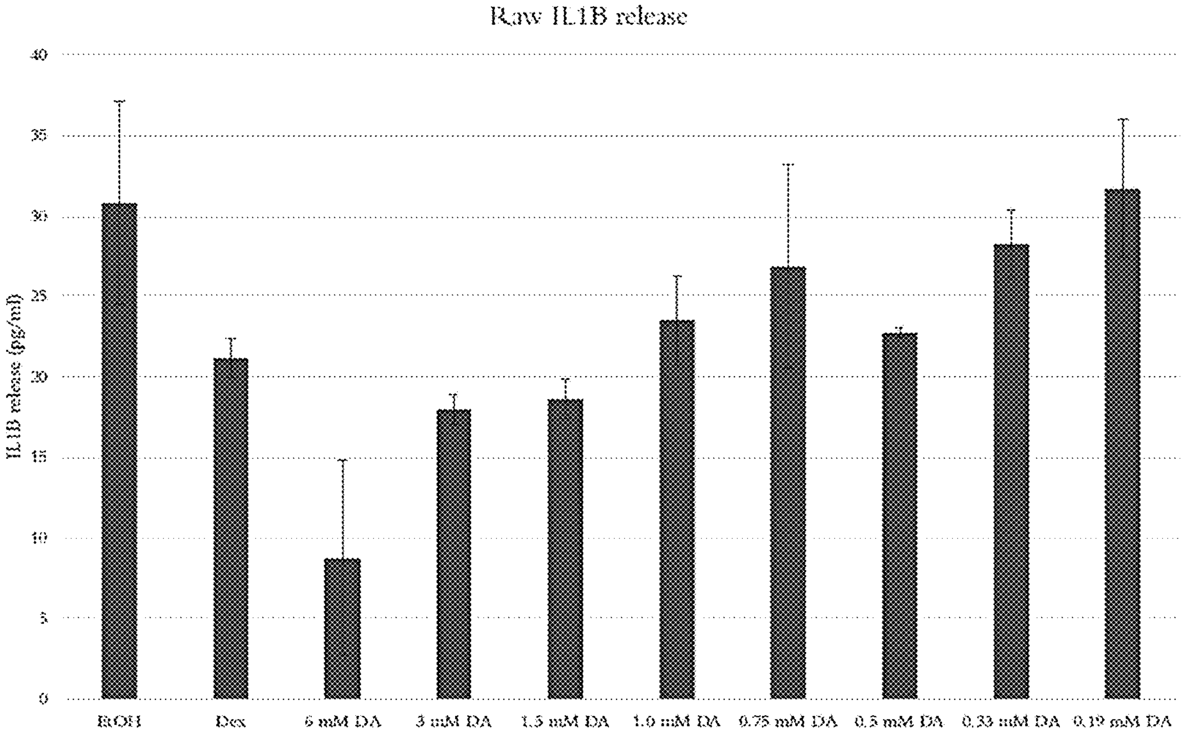
FIG. 4 is a bar graph that depicts concentrations of IL-1beta from cultures of THP-1 monocyte cells that were differentiated into macrophage-like cells with phorbol 12-myristate 13-acetate (PMA) and then exposed to ethanol vehicle, dexamethasone (Dex) positive control, or decanoic acid at concentrations ranging from 0.19 millimolar to 6 millimolar. The graph displays a dose-dependent inhibition of IL-1beta concentrations in cultures treated with decanoic acid.
Figure 5A:
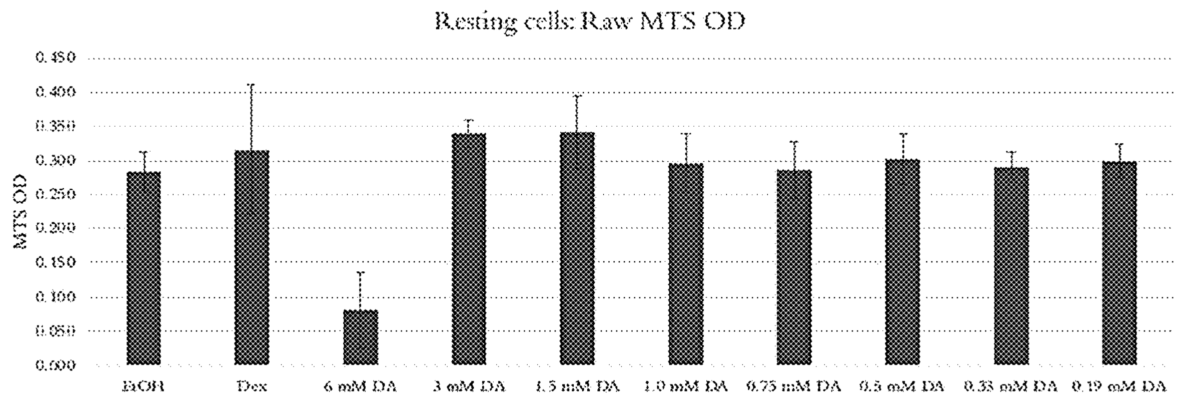
FIGS. 5A and 5B are bar graphs that depict the viability of THP-1 cells that were differentiated into macrophage-like cells with PMA and then exposed to ethanol vehicle, dexamethasone positive control, or decanoic acid at concentrations ranging from 0.19 millimolar to 6 millimolar.
Figure 5B:
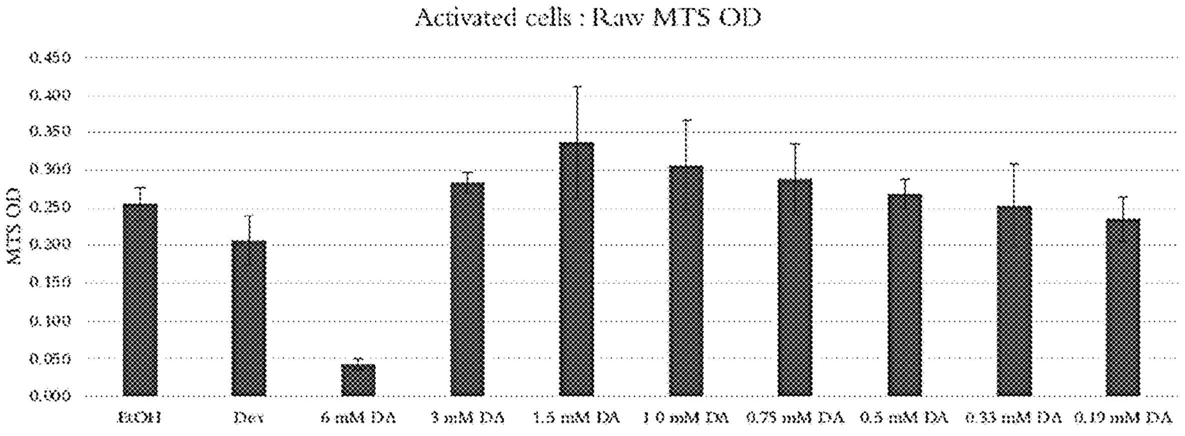

Cells cultured with decanoic acid displayed a dose-dependent inhibition of IL-1beta release. 1.5 and 3 millimolar concentrations of decanoic acid displayed superior inhibition relative to the steroid dexamethasone, which was statistically significant (FIG. 4). Resting cells did not release detectable IL-1beta. Response did not correlate with viability. Similar results were observed for activation with the TLR7 agonist CL075 instead of LPS. These results suggest that decanoic acid can inhibit monocyte- and macrophage-mediated inflammation.

Cell viability was also assessed by optical density at 490 nanometers (FIGS. 5A & 5B). 6 mM decanoic acid displayed an unfavorable effect on viability, which suggests a narrow therapeutic window for decanoic acid.

Example 4. Topical Anti-Inflammatory and Analgesic Composition Comprising Decanoic Acid, Tryptophan, and Other Amino Acids 500 milligrams of each of tryptophan, cysteine, methionine, lysine, arginine, histidine, and tyrosine are weighed and combined in a first 50-milliliter polypropylene tube. 20 milliliters of glycerin are pipetted into the first tube, and the amino acids are mixed into the glycerin by vortexing.

344 milligrams of decanoic acid is weighed and added into a second 50-milliliter polypropylene tube. 8.5 milliliters of MIGLYOL® 812, 3.8 milliliters of isopropyl myristate, and 5.25 milliliters of SEPINEO® P 600 are pipetted into the second tube, and the decanoic acid is mixed into the liquids by vortexing. MIGLYOL® 812 consists of triglycerides that comprise esters of octanoic acid at a concentration of 50-80 percent by mass and esters of decanoic acid at a concentration of 20-50 percent by mass, in which all of the triglycerides are esters of octanoic acid and/or decanoic acid.

The first and second polypropylene tubes are incubated at 37 degrees Celsius in a shaker oven overnight.

29 milliliters of phosphate buffered saline (PBS) is pipetted into a third 50-milliliter polypropylene tube, and 30 milliliters of propylene glycol is pipetted into a fourth 50-milliliter polypropylene tube.

The contents of the first, second, third, and fourth tubes are poured into a blender and blended to emulsify the aqueous and lipid phases. The total volume of the composition is about 100 milliliters.

The foregoing composition is useful as a topical anti-inflammatory, analgesic composition to partition decanoic acid, tryptophan, cysteine, methionine, lysine, arginine, histidine, and tyrosine across the skin and into underlying subcutaneous tissue.

Example 5. Topical Anti-Inflammatory and Analgesic Composition Comprising Decanoic Acid and Tryptophan 80 milliliters of glycerin, 120 milliliters of propylene glycol, and 116 milliliters of PBS are combined into a first solution. 10.8 grams of tryptophan is weighed, added to the first solution, and mixed well.

34 milliliters of MIGLYOL® 812, 15.2 milliliters of isopropyl myristate, and 21 milliliters of SEPINEO® P 600 are combined into a second solution. 1.376 grams of decanoic acid is weighed, added into the second solution, and mixed well.

The first and second solutions are incubated at 37 degrees Celsius in a shaker oven overnight. The first and second solutions are then combined in a blender with 4 grams of titanium dioxide, and the mixture is blended to emulsify the aqueous and lipid phases. The total volume of the composition is about 400 milliliters.

The foregoing composition is useful as a topical anti-inflammatory, analgesic composition to partition decanoic acid and tryptophan across the skin and into underlying subcutaneous tissue.

Example 6. Topical Anti-Inflammatory and Analgesic Composition Comprising Decanoic Acid, Tryptophan, and Glutamate 80 milliliters of glycerin, 120 milliliters of propylene glycol, and 116 milliliters of PBS are combined into a first solution. 10.8 grams of tryptophan and 1.177 grams of glutamic acid are weighed, added to the first solution, and mixed well.

34 milliliters of MIGLYOL® 812, 15.2 milliliters of isopropyl myristate, and 21 milliliters of SEPINEO® P 600 are combined into a second solution. 1.376 grams of decanoic acid is weighed, added into the second solution, and mixed well.

The first and second solutions are incubated at 37 degrees Celsius in a shaker oven overnight. The first and second solutions are then combined in a blender with 4 grams of titanium dioxide, and the mixture is blended to emulsify the aqueous and lipid phases. The total volume of the composition is about 400 milliliters.

The foregoing composition is useful as a topical anti-inflammatory, analgesic composition to partition decanoic acid, tryptophan, and glutamic acid across the skin and into underlying subcutaneous tissue.

Example 7. Use of Topical Composition to Treat Knee Pain in Human Subjects

The composition according to Example 5 was administered to a human subject suffering from knee pain associated with osteoarthritis. The subject reported an analgesic effect with a duration of about 6-7 hours.

Example 8. Use of Topical Composition to Treat Back Pain in Human Subjects

The composition according to Example 5 was administered to a human subject suffering from back pain, and the subject reported that the composition displayed efficacy at treating the back pain.

Example 9. Use of Topical Composition to Treat Peripheral Neuropathy in Human Subjects The composition according to Example 5 was administered to a human subject suffering from diabetic peripheral neuropathy, and the subject reported that the composition displayed efficacy at treating pain associated with the diabetic peripheral neuropathy.

Example 10. Use of Topical Composition to Treat Plaque Psoriasis in Human Subjects The composition according to Example 5 was administered to a human subject suffering from plaque psoriasis, and the subject reported that the composition displayed efficacy at treating pain and inflammation associated with the plaque psoriasis.

Example 11. Use of Topical Composition to Treat Herpes Simplex in Human Subjects The composition according to Example 5 was administered to a human subject suffering from herpes simplex virus lesions on the lip, and the subject reported that the composition displayed efficacy at treating pain associated with the lesions.

Example 12. Use of Topical Composition to Treat Chemotherapy-Induced Peripheral Neuropathy (CIPN) in Human Subjects The composition according to Example 5 was administered to a human subject suffering from CIPN, and the subject reported that the composition displayed efficacy at treating pain associated with the CIPN.

What is claimed is:

1. A method to treat inflammation in a subject, comprising:

providing the anti-inflammatory composition comprising a free fatty acid, a carboxylate, free tryptophan, water, and one or more alcohols, wherein: the free fatty acid has a conjugate base, which is the carboxylate;

the composition comprises a combinedconcentration of the free fatty acid and the carboxylate of at least 300 parts per million and up to 3 percent by mass, the composition comprises the free tryptophan at a concentration of at least 2,700 parts per million and up to 10 percent by mass;

the composition comprises the water at a concentration of at least 10 percent and up to 50 percent by mass;

the composition comprises the one or more alcohols at a concentration of at least 30 percent and up to 70 percent by mass; and topically administering an effective amount of the composition to skin of the subject, wherein the administering provides an analgesic effect.

2. A method to treat pain associated with osteoarthritis, comprising:

providing the anti-inflammatory composition of claim 1;

identifying a subject who presents with osteoarthritis or a symptom of osteoarthritis, wherein the osteoarthritis or the symptom is localized to a joint of the subject; and topically administering an effective amount of the composition to skin of the joint, wherein the effective amount is effective to treat the pain that is localized to the joint.

3. The method of claim 2, wherein the joint is a knee.

4. A method of treating pain or inflammation in a subject, comprising topically administering an effective amount of the anti-inflammatory composition of claim 1 to skin of the subject, wherein:

the effective amount is effective to reduce interleukin-1 beta (IL-1β) and the effective amount is effective to inhibit inflammasome-mediated signaling.

5. The method of claim 4, wherein:

the effective amount is effective to reduce IL-1β release from macrophage-like cells.

6. A method to re-differentiate osteoarthritic chondrocytes, comprising treating osteoarthritic chondrocytes with an effective amount of the anti-inflammatory composition of claim 1, wherein:

treating increases expression of one or more of SOX9, aggrecan (ACAN), or collagen type II alpha (Col2a1) in the osteoarthritic chondrocytes.

7. The method of claim 1, wherein the effective amount is about 50 milligrams to about 10 grams.

8. The method of claim 4, wherein the free fatty acid is decanoic acid, and the carboxylate is decanoate.

9. The method of claim 4, wherein the composition comprises a combined concentration of the free fatty acid and the carboxylate of at least 1,000 parts per million and up to 1.5 percent by mass.

10. The method of claim 1, wherein the free fatty acid is a saturated fatty acid comprising at least 6 and up to 14 carbon atoms.

11. The method of claim 1, wherein the composition comprises triglycerides at a concentration of at least 2 percent and up to 25 percent by mass, the triglycerides comprise esters of octanoic acid at a concentration of at least 50 percent and up to 80 percent by mass, and the triglycerides comprise esters of decanoic acid at a concentration of at least 20 percent and up to 50 percent by mass.

* * * * *